(12) United States Patent
Chen et al.

(10) Patent No.: US 11,948,531 B2
(45) Date of Patent: Apr. 2, 2024

(54) LIGHT SOURCE DEVICE AND DISPLAY DEVICE ALTERNATELY EMITTING LIGHT BEAMS

(71) Applicant: Industrial Technology Research Institute, Hsinchu (TW)

(72) Inventors: Tzung-Te Chen, Taipei (TW); Hsin-Yun Tsai, Hsinchu County (TW); Shih-Yi Wen, Hsinchu (TW); Chia-Fen Hsieh, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 17/565,495

(22) Filed: Dec. 30, 2021

(65) Prior Publication Data

US 2022/0406271 A1 Dec. 22, 2022

Related U.S. Application Data

(60) Provisional application No. 63/212,724, filed on Jun. 21, 2021.

(30) Foreign Application Priority Data

Dec. 22, 2021 (TW) ................. 110148157

(51) Int. Cl.
*G09G 5/10* (2006.01)
*G09G 5/02* (2006.01)
(Continued)

(52) U.S. Cl.
CPC ............... *G09G 5/026* (2013.01); *H04R 3/00* (2013.01); *A61N 5/0622* (2013.01);
(Continued)

(58) Field of Classification Search
CPC ........ G09G 5/026; H04R 3/00; A61N 5/0622; A61N 2005/0663
(Continued)

(56) References Cited

U.S. PATENT DOCUMENTS 10,159,816 B2 12/2018 Tsai et al.
10,265,497 B2 4/2019 Tsai et al.
(Continued)

FOREIGN PATENT DOCUMENTS

CN 103096581 5/2013
CN 103442765 12/2013
(Continued)

OTHER PUBLICATIONS

K. Iwakiri, A. Yasukouchi and A. Murata, "Effects of spectral distribution of light on the arousal level in humans," IEEE SMC'99 Conference Proceedings. 1999 IEEE International Conference on Systems, Man, and Cybernetics (Cat. No. 99CH37028), Tokyo, Japan, 1999, pp. 271-276 vol.2 (Year: 1999).*
(Continued)

*Primary Examiner* — Jonathan M Blancha
(74) *Attorney, Agent, or Firm* — JCIPRNET

(57) ABSTRACT

A light source device, including a first light source, providing a first light beam in a first time period of a first period; and a second light source, providing a second light beam in a second time period of the first period, is provided. The first light beam and the second light beam have the same color temperature. The first light beam and the second light beam are emitted alternately in the first period, and a color rendering index of mixed light of the first light beam and the second light beam is greater than or equal to 85.

26 Claims, 12 Drawing Sheets

(51) Int. Cl.
*H04R 3/00* (2006.01)
*A61N 5/06* (2006.01)

(52) U.S. Cl.
CPC .. *A61N 2005/0663* (2013.01); *G09G 2380/08* (2013.01); *H04R 2499/15* (2013.01)

(58) Field of Classification Search
USPC ........................................................ 345/690
See application file for complete search history.

(56) References Cited

U.S. PATENT DOCUMENTS

| | | | |
|---|---|---|---|
| 10,279,192 | B2 | 5/2019 | Malchano et al. |
| 10,293,177 | B2 | 5/2019 | Malchano et al. |
| 10,307,611 | B2 | 6/2019 | Malchano et al. |
| 10,682,490 | B2 | 6/2020 | Tsai et al. |
| 10,702,705 | B2 | 7/2020 | Malchano et al. |
| 10,843,006 | B2 | 11/2020 | Malchano et al. |
| 10,881,550 | B2 | 1/2021 | Tedford et al. |
| 2013/0020929 | A1* | 1/2013 | van de Ven ......... H01L 25/0753 313/498 |
| 2014/0036164 | A1* | 2/2014 | Narimatsu ............ H04N 9/3164 349/5 |
| 2017/0025481 | A1* | 1/2017 | Sung .................... H10K 59/353 |
| 2017/0368367 | A1* | 12/2017 | Sato ........................ H05B 45/00 |
| 2018/0133507 | A1* | 5/2018 | Malchano ............. A61B 5/0036 |
| 2018/0221683 | A1* | 8/2018 | Kang ...................... F21V 23/02 |
| 2019/0105509 | A1 | 4/2019 | Tsai et al. |
| 2019/0126062 | A1 | 5/2019 | Adaikkan et al. |
| 2020/0164220 | A1* | 5/2020 | Broeng ................ A61N 5/0622 |

FOREIGN PATENT DOCUMENTS

| | | |
|---|---|---|
| JP | 2008034188 | 2/2008 |
| TW | 202015491 | 4/2020 |
| TW | 202106115 | 2/2021 |

OTHER PUBLICATIONS

Maiken Nedergaard et al., "Glymphatic failure as a final common pathway to dementia", Science., Author manuscript, PMC 2021, Jun. 2021, pp. 1-20.

Hannah F. Iaccarino et al., "Gamma frequency entrainment attenuates amyloid load and modifies microglia", Nature., Author manuscript, PMC 2017, Oct. 2017, pp. 1-37.

Anthony J. Martorell et al., "Multi-sensory gamma stimulation ameliorates Alzheimer's-associated pathology and improves cognition.", Cell., vol. 177, Apr. 2019, pp. 256-271.

Youli Yao et al., "Non-invasive 40-Hz Light Flicker Ameliorates Alzheimer's-Associated Rhythm Disorder via Regulating Central Circadian Clock in Mice", Frontiers in Physiology, vol. 11, Apr. 2020, pp. 1-11.

Annabelle C. Singer et al., "Noninvasive 40-Hz light flicker to recruit microglia and reduce amyloid beta load", Nature Protocols, vol. 13, Aug. 2018, pp. 1850-1868.

Chinnakkaruppan Adaikkan et al., "Gamma Entrainment Binds Higher-Order Brain Regions and Offers Neuroprotection Neuroprotection", Neuron., Author manuscript, PMC 2020, Jun. 2019, pp. 1-39.

"Office Action of Taiwan Counterpart Application", dated Sep. 19, 2022, p. 1-p. 6.

* cited by examiner

LIGHT SOURCE DEVICE AND DISPLAY DEVICE ALTERNATELY EMITTING LIGHT BEAMS

CROSS-REFERENCE TO RELATED APPLICATION

This application claims the priority benefit of U.S. Provisional Application No. 63/212,724, filed on Jun. 21, 2021, and Taiwan Application No. 110148157, filed on Dec. 22, 2021. The entirety of each of the above-mentioned patent applications is hereby incorporated by reference herein and made a part of this specification.

BACKGROUND

Technical Field

The disclosure relates to a light source device and a display device, and particularly relates to a light source device or a display device for giving visual stimulation with a fixed period/frequency.

Description of Related Art

Patients with Alzheimer's disease account for approximately 60% to 80% of the total number of patients with dementia. The pathological features of Alzheimer's disease include accumulation of abnormal proteins, such as amyloid plaque produced by β-amyloid between neurons, and neurofibrillary tangles formed by abnormal accumulation of tau protein in cells. The amyloid plaque may interfere with signals emitted by nerve synapses between the cells, and the neurofibrillary tangles may prevent nutrients from being transmitted in the cells, leading to cell death. Generally speaking, when glymphatic fluid, such as microglia and astrocyte, in the human body is functioning normally, the cerebrospinal fluid (CSF) may take away the accumulated abnormal proteins, and the abnormal proteins are metabolized by the liver. However, when the glymphatic fluid is not functioning normally, the accumulation of abnormal proteins in the brain cells cannot be eliminated, which eventually causes neurodegeneration to form Alzheimer's disease, causing dementia.

The current non-invasive stimulus signal for the treatment of Alzheimer's disease is to induce gamma brain waves by acousto-optic stimulation to activate the microglia, thereby eliminating the accumulation of abnormal proteins to alleviate cognitive decline. However, the current acousto-optic stimulus signal is extremely monotonous, long-term viewing or listening may easily cause fatigue or discomfort, and long-term application is difficult, which affects the willingness of the user to use.

SUMMARY

The disclosure provides a light source device, which can treat or alleviate diseases by giving visual stimulation with a specific period/frequency.

According to some embodiments of the disclosure, a light source device is provided, which includes a first light source, providing a first light beam in a first time period of a first period; and a second light source, providing a second light beam in a second time period of the first period. The first light beam and the second light beam are emitted alternately in the first period, and a color rendering index of mixed light of the first light beam and the second light beam is greater than or equal to 85.

According to other embodiments of the disclosure, a display device is provided, which includes a light source device. The light source device includes a first light source, providing a first light beam in a first time period of a first period; and a second light source, providing a second light beam in a second time period of the first period. The first light beam and the second light beam are emitted alternately in the first period, and a color rendering index of mixed light of the first light beam and the second light beam is greater than or equal to 85.

According to some embodiments of the disclosure, a light source device is provided, which includes a first light source, providing a first light beam in a first time period of a first period; and a second light source, providing a second light beam in a second time period of the first period. The first light beam and the second light beam are emitted alternately in the first period, and the first light beam and the second light beam have a same color temperature.

Based on the above, the disclosure provides the light source device and the display device, which give visual stimulation with a fixed period/frequency to treat diseases by providing a light period of a combination of at least two different light. The more comfortable light stimulation combination can overcome the current issues of boring non-invasive stimulus signal and difficulty in long-term application, and can be used in lighting and display of daily life.

DETAILED DESCRIPTION OF DISCLOSED EMBODIMENTS

Figure 1:
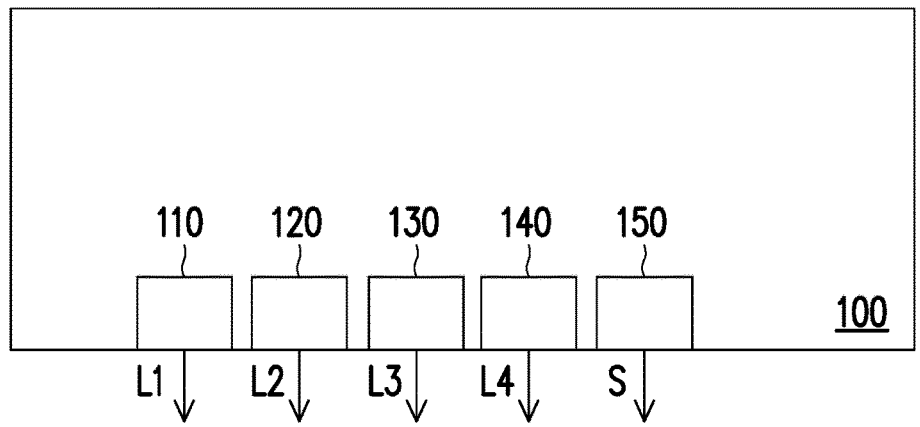
FIG. 1 is a schematic diagram of a light source device according to some embodiments of the disclosure.

Please refer to the following embodiments and accompanying drawings in order to fully understand the disclosure, but the disclosure can still be practiced in many different forms and should not be construed as being limited to the embodiments described herein. In the drawings, for the sake of clarity, components and relative sizes thereof may not be drawn according to actual scale.

Figure 2:
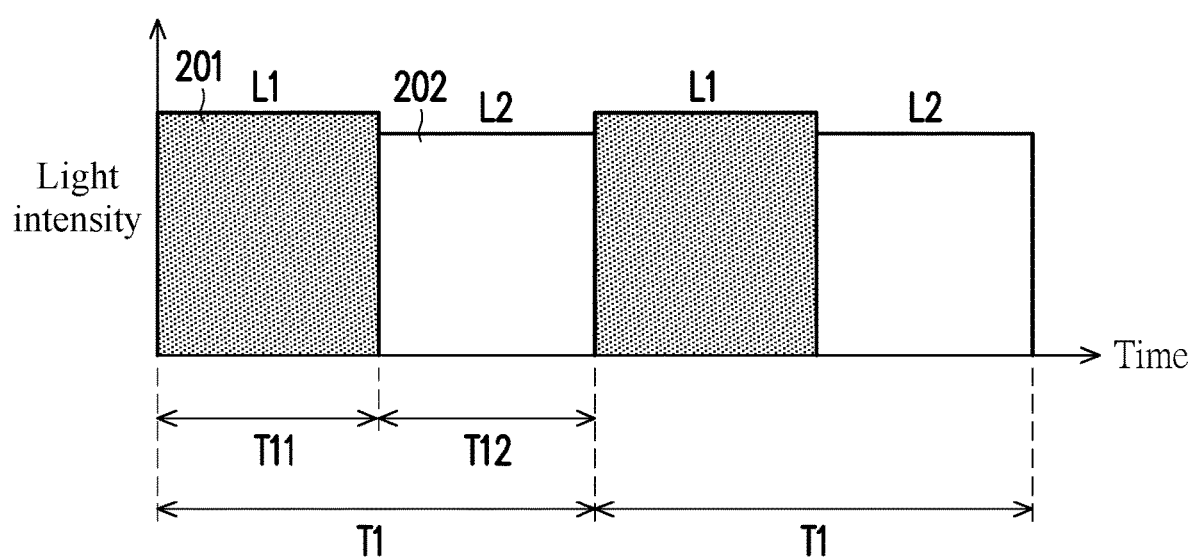
FIG. 2 to FIG. 6 are optical signal timing diagrams according to some embodiments of the disclosure.

FIG. 1 is a schematic diagram of a light source device according to some embodiments of the disclosure. FIG. 2 is an optical signal timing diagram according to some embodiments of the disclosure. Please refer to FIG. 1 and FIG. 2 at the same time. As shown in FIG. 1, a light source device 100 includes a first light source 110 and a second light source 120. According to some embodiments, the first light source 110 and the second light source 120 are array light emitting diodes or other elements that can emit light beams, and the disclosure is not limited thereto. The first light source 110 is configured to provide a first light beam L1, the second light source 120 is configured to provide a second light beam L2, and the first light beam L1 and the second light beam L2 are configured to be emitted alternately to provide light stimulation. As shown in FIG. 2, the first light source 110 is configured to provide a first light beam 201 in a first time period T11 of a first period T1, and the second light source 120 is configured to provide a second light beam 202 in a second time period T12 of the first period T1. The first time period T11 and the second time period T12 constitute the first period T1, and the first light beam 201 and the second light beam 202 are emitted alternately in the first period T1. According to some embodiments, a first frequency f1 corresponding to the first period T1 is 35-45 Hz, that is, f1=1/T1=35-45 Hz. According to some embodiments, the first frequency f1 corresponding to the first period T1 is 40 Hz, but the disclosure is not limited thereto. In the embodiment, the duration of the first time period T11 is equal to the duration of the second time period T12, that is, the first light beam 201 and the second light beam 202 have the same duty ratio, that is, T11/T1=T12/T1. In another embodiment, the first light beam 201 and the second light beam 202 may have different duty ratios.

In the embodiment, the first light beam 201 in the first time period T11 and the second light beam 202 in the second time period T12 are respectively continuous light beams. According to some embodiments, the wavelengths of the first light beam 201 and the second light beam 202 are between 380 nm and 1050 nm, and the disclosure is not limited thereto. According to some embodiments, the first light beam 201 and the second light beam 202 are monochromatic light, mixed light containing multiple monochromatic light, or full spectrum light, but not limited thereto.

In the embodiment, the first light beam 201 and the second light beam 202 have the same color temperature and the same spectrum. According to some embodiments, the color temperature of the first light beam 201 and the second light beam 202 is between 2000K to 7000K, but not limited thereto. According to some embodiments, the difference between the first light beam 201 and the second light beam 202 is that the first light beam 201 and the second light beam 202 have different light intensities, that is, the light intensity of the first light beam 201 may be greater than or less than the light intensity of the second light beam 202.

In the embodiment, a light intensity difference between the first light beam 201 and the second light beam 202 is less than a threshold. If the light intensity of the first light beam 201 is I1 and the light intensity of the second light beam 202 is I2, a light intensity difference D is defined as D=|I1−I2|/I1+I2. According to some embodiments, the light intensity difference D between the first light beam 201 and the second light beam 202 is less than 10%. In some embodiments, the light intensity difference D between the first light beam 201 and the second light beam 202 is less than 5%. In some embodiments, the light intensity difference D between the first light beam 201 and the second light beam 202 is less than 2.5%.

When the first light beam 201 and the second light beam 202 are sequentially emitted in the first period T1, since the color temperature and the spectrum of the first light beam 201 and the second light beam 202 are the same, and there is only difference in light intensities, the first light beam 201 and the second light beam 202 emitted by the light source device 100 respectively flicker with different light intensities but the same first frequency f1 to provide light stimulation, and the mixed light of the first light beam 201 and the second light beam 202 has a high color rendering index (CRI), that is, CRI≥85. Since the difference between the light intensities of the first light beam 201 and the second light beam 202 is only less than the threshold, for example, the difference between the light intensities of the first light beam 201 and the second light beam 202 is less than 10% or less, for a patient to be treated, the received light intensity change is relatively small, which can reduce the burden on the eyes of the patient. By changing an irradiation period of the first light beam 201 and the second light beam 202 emitted by the first light source 110 and the second light source 120 in the light source device 100, light stimulation received by the patient may be adjusted, for example, when f1=35-45 Hz, thereby inducing gamma brain waves to activate microglia. In subsequent embodiments, various implementations will be explained one by one.

Figure 3:
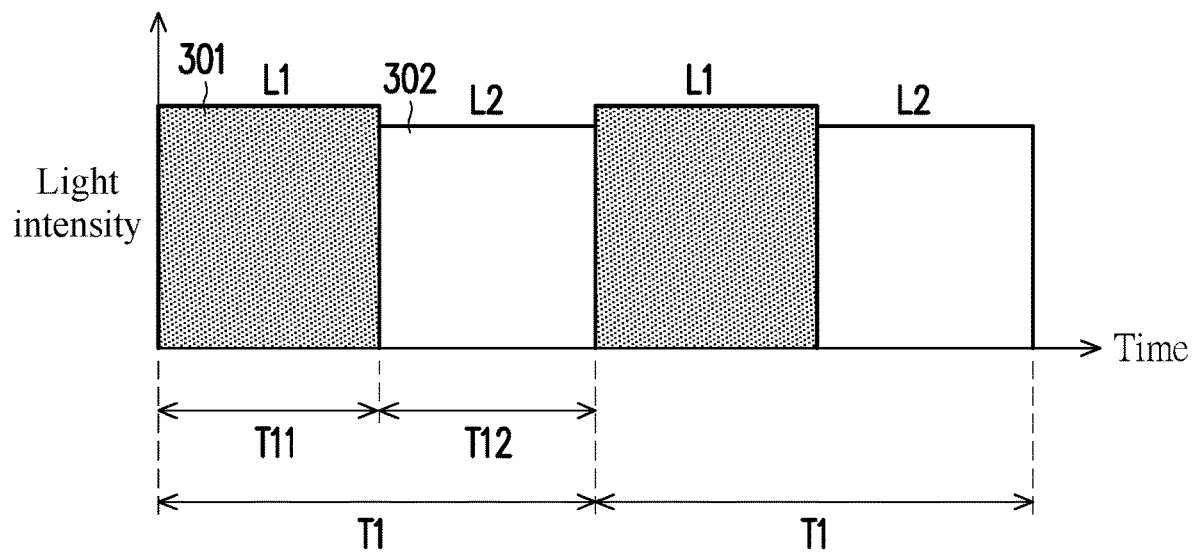

FIG. 3 is an optical signal timing diagram according to some embodiments of the disclosure. The optical signal timing diagram shown in FIG. 3 is similar to FIG. 2. The first light source 110 provides a first light beam 301 in the first time period T11 of the first period T1, and the second light source 120 is configured to provide a second light beam 302 in the second time period T12 of the first period T1. The light intensity difference between the first light beam 301 and the second light beam 302 is less than a threshold, for example, less than 10% or less.

The difference between FIG. 3 and FIG. 2 is that the first light beam 301 and the second light beam 302 have the same color temperature, but the second light beam 302 has a different spectrum from the first light beam 301. In other words, the first light beam 301 and the second light beam 302 have different wavelength compositions, and the first light beam 301 and the second light beam 302 are irradiated alternately in the first period T1. In another embodiment, the first light beam 301 and the second light beam 302 are mixed into light with a high color rendering index (for example, CRI≥85), and when f1=35-45 Hz, the patient is visually stimulated to induce gamma brain waves. Since the first light beam 301 and the second light beam 302 have the same color temperature but different spectra, the first light beam 301 and the second light beam 302 may have different light intensities for different usage purposes. In some embodiments, if the light source device 100 is used as a display, the first light beam 301 and the second light beam 302 may have the same light intensity to prevent the user from seeing a screen with changing brightness. In other embodiments, if the light source device 100 is used to provide illumination, the first light beam 301 and the second light beam 302 may have different light intensities, and the light intensity difference is less than a threshold, for example, less than 10% or less, so that the user receives light stimulation with changes in brightness.

Figure 4:
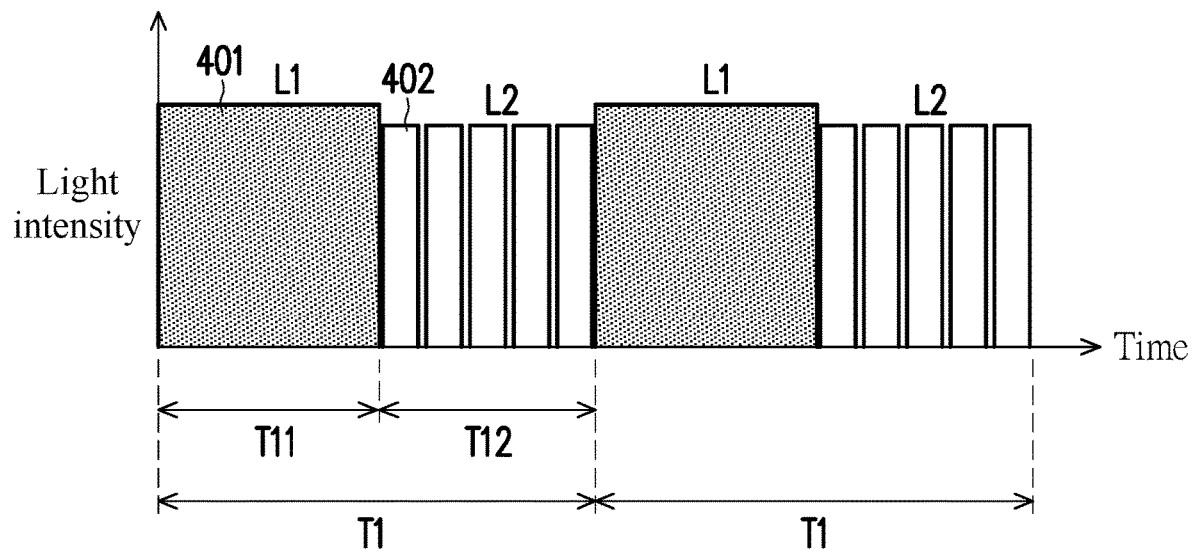

FIG. 4 is an optical signal timing diagram according to some embodiments of the disclosure. The optical signal timing diagram shown in FIG. 4 is similar to FIG. 2. The first light source 110 provides a first light beam 401 in the first time period T11 of the first period T1, and the second light source 120 is configured to provide a second light beam 402 in the second time period T12 of the first period T1. The light intensity difference between the first light beam 401 and the second light beam 402 is less than a threshold, for example, less than 10% or less. In addition, the first light beam 401 and the second light beam 402 have the same color temperature and the same spectrum. In other embodiments, the first light beam 401 and the second light beam 402 have the same color temperature but different spectra.

The difference between FIG. 4 and FIG. 2 is that one of the first light beam 401 and the second light beam 402 is a continuous light beam, and the other one is a flicker light beam with a flicker frequency, which is also referred to as a pulse width modulation (PWM) beam. In the embodiment, the first light beam 401 is a continuous light beam in the first time period T11, the second light beam 402 is a flicker light beam with a flicker frequency in the second time period T12, and the first light beam 401 and the second light beam 402 are mixed into light with a high color rendering index (CRI≥85). In other embodiments, the second light beam 402 is a continuous light beam in the second time period T12, and the first light beam 401 is a flicker light beam with a flicker frequency in the first time period T11, and the disclosure is not limited thereto. According to some embodiments, a flicker frequency range of the second light beam 402 in the second time period T12 is >500 Hz, and preferably 500-2000 Hz, but not limited thereto. In the embodiment, the duration of the first time period T11 is equal to the duration of the second time period T12, and the sum of the duration of the first time period T11 and the duration of the second time period T12 is equal to the duration of the first period, that is, the first time period T11 and the second time period T12 respectively account for 50% of the first period T1. In another embodiment, the first time period T11 or the second time period T12 may account for 40-60% of the first period T1, but not limited thereto. When the flicker frequency range of the second light beam 402 is 500-2000 Hz, the frequency has exceeded the recognition frequency of the human eye. Therefore, although the second light beam 402 is a flicker light beam, the patient cannot easily perceive the flickering of the beam. In the embodiment, the first light beam 401 generated by the light source device 100 in the first time period T11 of the first period T1 may provide light stimulation of a continuous light beam, and the second light beam 402 generated in the second time period T12 of the first period T1 may provide light stimulation of a flicker light beam.

Figure 5:
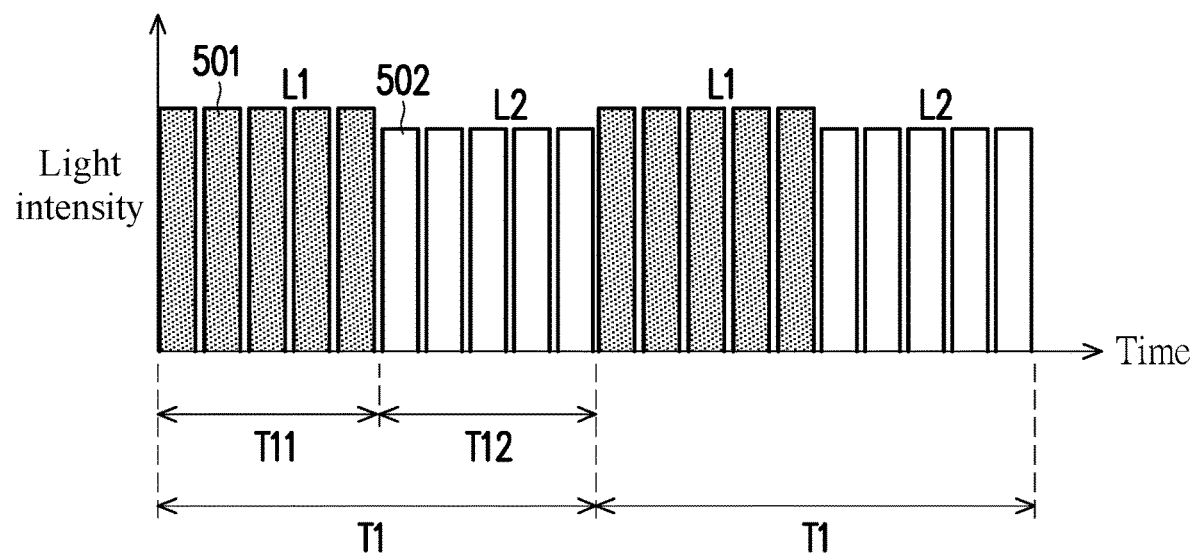

FIG. 5 is an optical signal timing diagram according to some embodiments of the disclosure. The optical signal timing diagram shown in FIG. 5 is similar to FIG. 4. The first light source 110 provides a first light beam 501 in the first time period T11 of the first period T1, and the second light source 120 is configured to provide a second light beam 502 in the second time period T12 of the first period T1. The first light beam 501 and the second light beam 502 have different light intensities, and the light intensity difference is less than a threshold, for example, less than 10% or less. In addition, the first light beam 501 and the second light beam 502 have the same color temperature and the same spectrum, and are mixed into light with a high color rendering index (CRI≥85).

The difference between FIG. 5 and FIG. 4 is that the first light beam 501 in the first time period T11 and the second light beam 502 in the second time period T12 are both flicker light beams with flicker frequencies, the first light beam 501 has a first flicker frequency, and the second light beam 502 has a second flicker frequency. In an embodiment, the first flicker frequency of the first light beam 501 is different from the second flicker frequency of the second light beam 502. In another embodiment, the first flicker frequency of the first light beam 501 is the same as the second flicker frequency of the second light beam 502, and the disclosure is not limited thereto. According to some embodiments, flicker frequency ranges of the first light beam 501 and the second light beam 502 are respectively >1000 Hz, and preferably 1000-2000 Hz, but not limited thereto. According to some embodiments, the first light beam 501 and the second light beam 502 may have the same duty ratio or different duty ratios. According to some embodiments, the duty ratio of the first light beam 501 and the second light beam 502 is 40-60%, and preferably 50%, but not limited thereto. In the embodiment, the first light beam 501 provided by the light source device 100 in the first time period T11 of the first period T1 and the second light beam 502 provided in the second time period T12 of the first period T1 may both provide light stimulation of flicker light beams.

Figure 6:
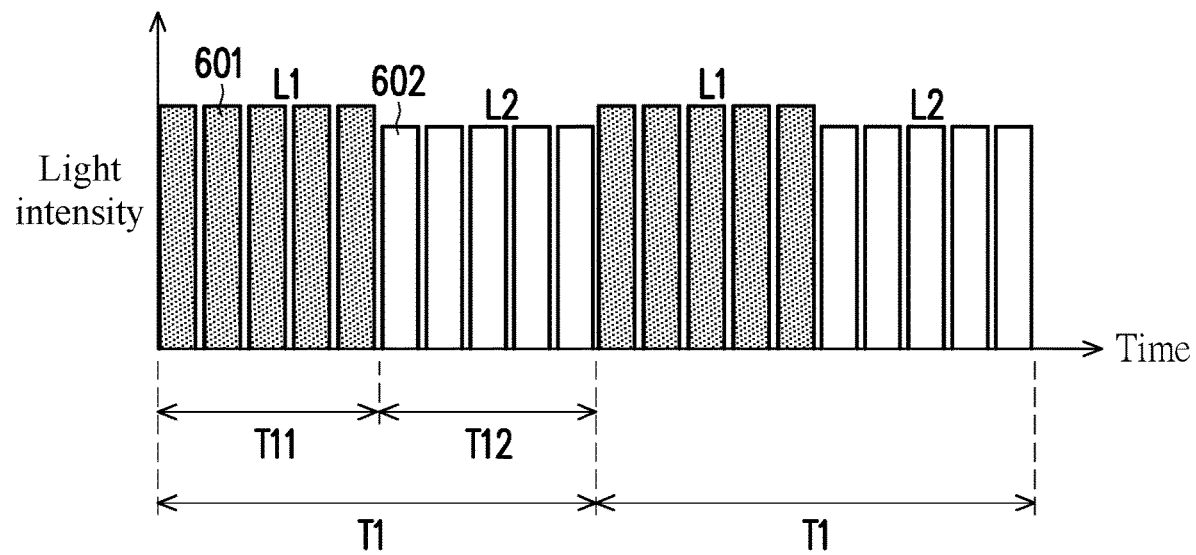

FIG. 6 is an optical signal timing diagram according to some embodiments of the disclosure. The optical signal timing diagram shown in FIG. 5 is similar to FIG. 6. The first light source 110 provides a first light beam 601 in the first time period T11 of the first period T1, and the second light source 120 is configured to provide a second light beam 602 in the second time period T12 of the first period T1. The light intensity difference between the first light beam 601 and the second light beam 602 is less than a threshold, for example, less than 10% or less.

The difference between FIG. 6 and FIG. 5 is that the first light beam 601 and the second light beam 602 have the same color temperature but different spectra. Therefore, in the embodiment, the light beams provided by the light source device 100 in the first period T1 are light beams that have the same color temperature but different spectra in the first period T1 and are emitted alternately to be mixed into light with a high color rendering index (CRI≥85) to generate visual stimulation to the patient. Since the first light beam 601 and the second light beam 602 have the same color temperature but different spectra, the first light beam 601 and the second light beam 602 may have different light intensities for different usage purposes. In some embodiments, if the light source device 100 is used as a display, the first light beam 601 and the second light beam 602 may have the same light intensity to prevent the user from seeing a screen with changing brightness. In other embodiments, if the light source device 100 is used to provide illumination, the first light beam 601 and the second light beam 602 may have different light intensities, and the light intensity difference is less than a threshold, for example, less than 10% or less, so that the user receives light stimulation with changes in brightness.

In the embodiments of FIG. 2 to FIG. 6, one of the first light beams 201, 301, 401, 501, and 601 and the second light beams 202, 302, 402, 502, and 602 may be white light or equal energy white light in a wavelength range or have a continuous spectrum in a wavelength range. According to some embodiments, the equal energy white light may be that each wavelength has the same energy in a given wavelength range, for example, all wavelengths have the same energy in a range of 400-800 nm. According to some embodiments, there is a continuous spectrum in a wavelength range, and the energy of each wavelength may be different in a given wavelength range, for example, all wavelengths have different energies in the range of 400-800 nm.

Figure 7:
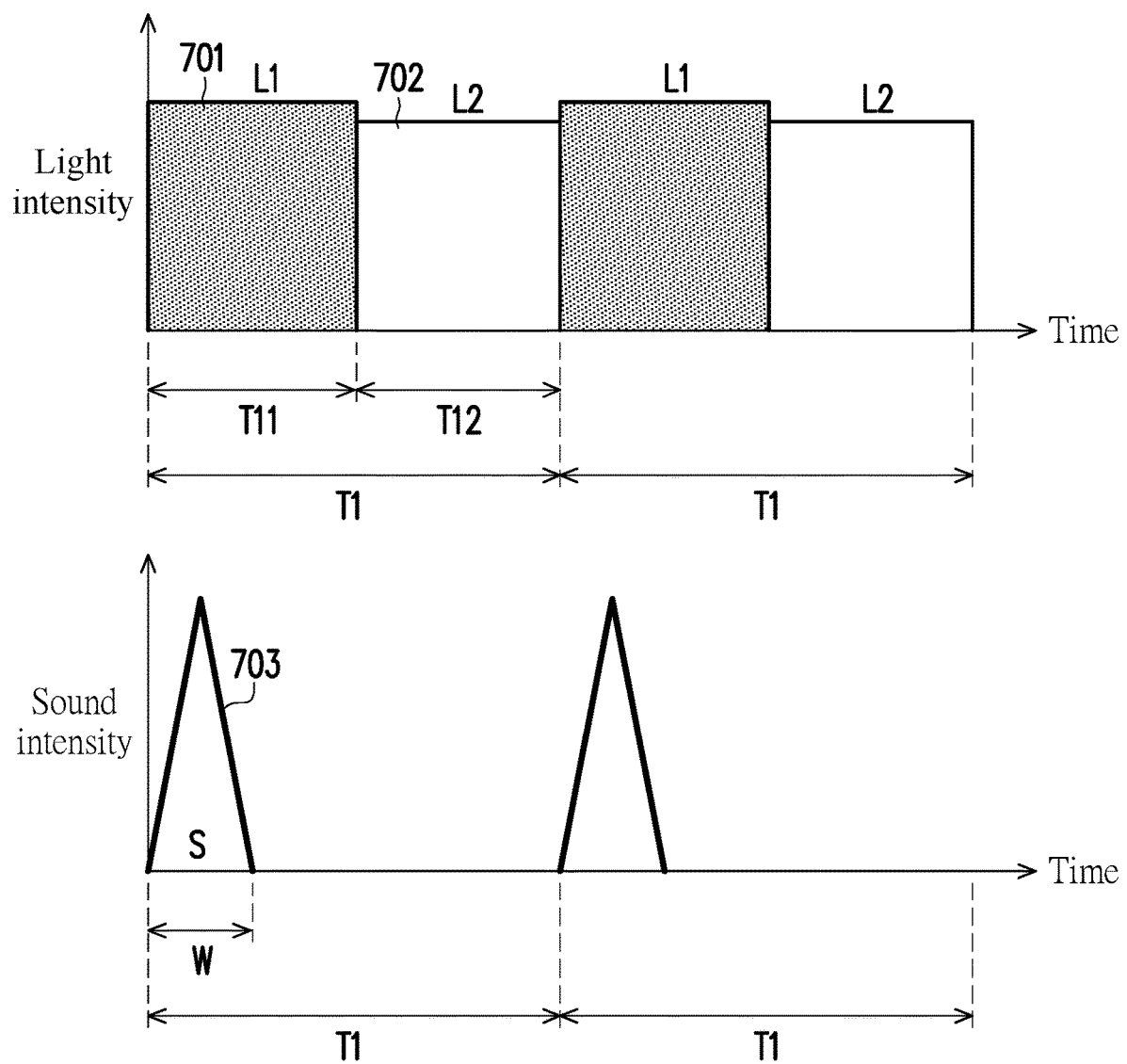
FIG. 7 is an acousto-optic signal timing diagram according to some embodiments of the disclosure.

FIG. 7 is an acousto-optic signal timing diagram according to some embodiments of the disclosure. Please refer to FIG. 1 and FIG. 7 at the same time. According to some embodiments, the light source device 100 further includes a sound source 150 for generating a sound wave pulse S. An emission period of the sound wave pulse S is the same as the first period T1. As shown in FIG. 7, in the first time period T11 of the first period T1, the first light source 110 emits a first light beam 701, and in the second time period T12 of the first period T1, the second light source 120 emits a second light beam 702. The first light beam 701 and the second light beam 702 here may be the various embodiments described in FIG. 2 to FIG. 6, so there will be no repetition. The first light beam 701 and the second light beam 702 may also be a combination of other embodiments mentioned below and are not limited thereto. On the other hand, in the first period T1, the sound source 150 emits a sound wave pulse 703 with a width W. According to some embodiments, the sound wave pulse 703 may be at any position in the first period T1, for example, in the first time period T11, in the second time period T12, or partially in the first time period T11 and partially in the second time period T12. According to some embodiments, the time length of the sound wave pulse 703 is less than the first period T1, and preferably 0.1-0.25 T1, and the disclosure is not limited thereto. Therefore, in the first period T1, there is not only light stimulation of the first light beam 701 and the second light beam 702, but also sound stimulation generated by the sound wave pulse 703 emitted by the sound source. Therefore, in the first period T1, the light source device 100 may provide acousto-optic stimulation at the same time to enhance stimulation to the brain of the user.

Figure 8A:
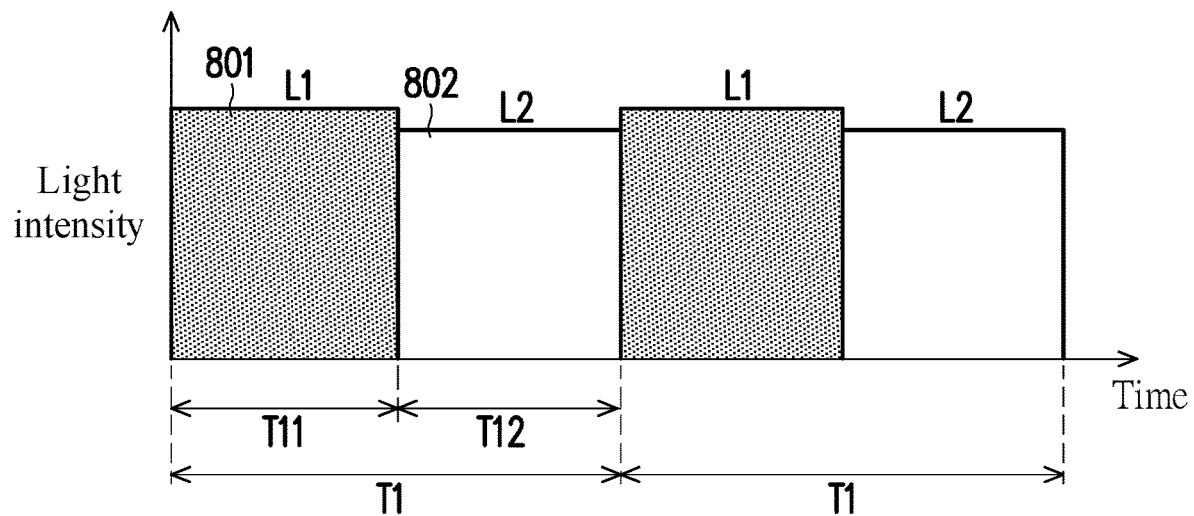
FIG. 8A to FIG. 8C are optical signal timing diagrams according to some embodiments of the disclosure.
Figure 8B:
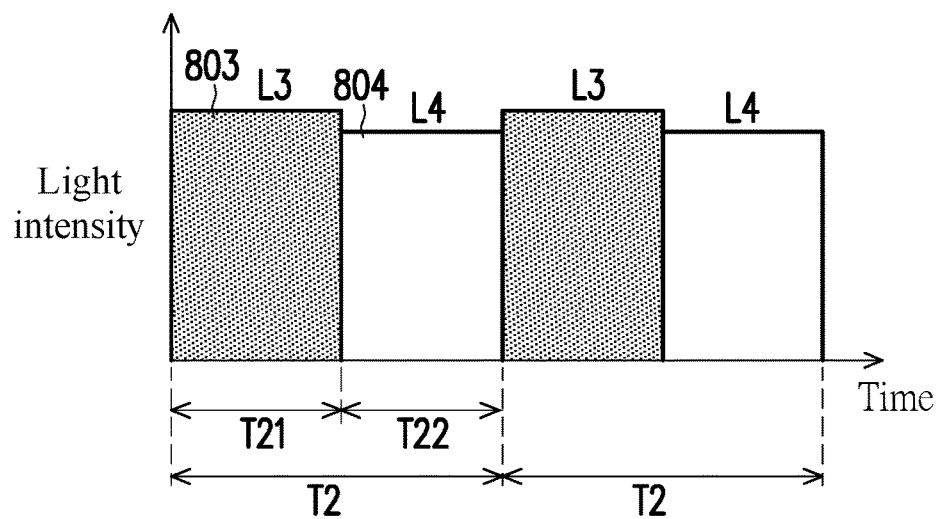
Figure 8C:
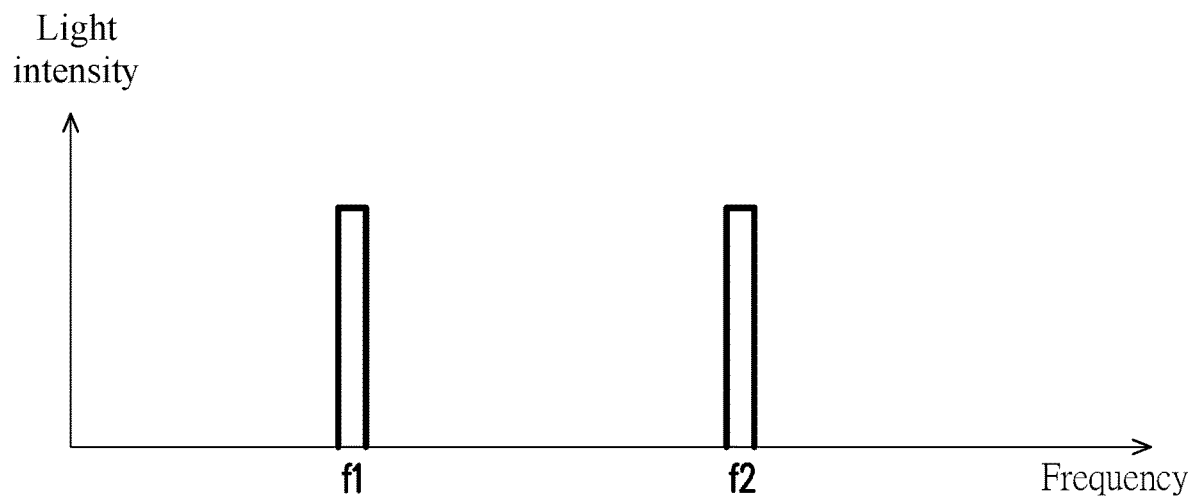

FIG. 8A to FIG. 8C are optical signal timing diagrams according to some embodiments of the disclosure. Please refer to FIG. 1 and FIG. 8A to FIG. 8C at the same time. The optical signal timing diagram shown in FIG. 8A is similar to FIG. 2. The first light source 110 provides a first light beam 801 in the first time period T11 of the first period T1, and the second light source 120 is configured to provide a second light beam 802 in the second time period T12 of the first period T1. The first light beam 801 and the second light beam 802 have different light intensities, and the light intensity difference between the two is less than a threshold, for example, less than 10% or less.

As shown in FIG. 1, the light source device 100 further includes a third light source 130 and a fourth light source 140. The third light source 130 is configured to provide a third light beam L3, and the fourth light source is configured to provide a fourth light beam L4. The third light source 130 and the fourth light source 140 are similar to the first light source 110 and the second light source 120 and are configured to be emitted alternately to generate light stimulation, and at least one set of the beams (L1+L2 or L3+L4) may be mixed into light with a high color rendering index (CRI≥85). According to some embodiments, the third light beam L3 and the fourth light beam L4 may have different light intensities, and the light intensity difference is less than a threshold, for example, less than 10% or less. According to some embodiments, the third light source 130 and the fourth light source 140 are array light emitting diodes or other elements that may emit similar beams, and the disclosure is not limited thereto. As shown in FIG. 8B, the third light source 130 is configured to provide a third light beam 803 in a third time period T21 of a second period T2. The fourth light source 140 is configured to provide a fourth light beam 804 in a fourth time period T22 of the second period T2, and the third light beam 803 and the fourth light beam 804 are emitted alternately in the second period T2. In the embodiment, the duration of the third time period T21 is equal to the duration of the fourth time period T22, and the sum of the duration of the third time period T21 and the duration of the fourth time period T22 is equal to the duration of the second period, that is, the third time period T21 and the fourth time period T22 respectively account for 50% of the second period T2. According to some embodiments, a second frequency f2 corresponding to the second period T2 may be different from the first frequency f1 corresponding to the first period T1. According to some embodiments, the second frequency f2 corresponding to the second period T2 is 55-65 Hz, that is, f2=1/T2=55-65 Hz, as shown in FIG. 8C. According to some embodiments, the second frequency f2 corresponding to the second period T2 is 60 Hz, and the disclosure is not limited thereto. According to some embodiments, the duration of the third time period T21 and the duration of the fourth time period T22 may be equal or unequal, and the disclosure is not limited thereto.

In the embodiment, the first light beam 801 and the second light beam 802 may be the various embodiments described in FIG. 2 to FIG. 6 or a combination of other embodiments mentioned below and are not limited thereto, so there will be no repetition. The third light beam 803 and the fourth light beam 804 here may be the various embodiments described in FIG. 2 to FIG. 6 or a combination of other embodiments mentioned below and are not limited thereto. In some embodiments, the first light beam 801 and the second light beam 802 have the same first color temperature, and the mixed light of the first light beam 801 and the second light beam 802 has a high color rendering index (CRI≥85). The third light beam 803 and the fourth light beam 804 have the same second color temperature, and the mixed light of the third light beam 803 and the fourth light beam 804 has a high color rendering index (CRI≥85). In other embodiments, the mixed light of the first light beam 801 and the second light beam 802 has a high color rendering index (for example, CRI≥85), but the mixed light of the third light beam 803 and the fourth light beam 804 may not have a high color rendering index (for example, CRI≥<85). According to some embodiments, the first color temperature and the second color temperature may be the same or different, and the disclosure is not limited thereto. According to some embodiments, when the first color temperature is the same as the second color temperature, the spectra of the first light beam 801, the second light beam 802, the third light beam 803, and the fourth light beam 804 are all different.

When the light source device 100 emits two sets of light with different periods or frequencies at the same time, for example, the first period T1 and the second period T2 in FIG. 8A to FIG. 8C, the light source device 100 may perform light stimulation with two different frequencies on the patient, which increases stimulation of the brain of the patient.

Figure 9:
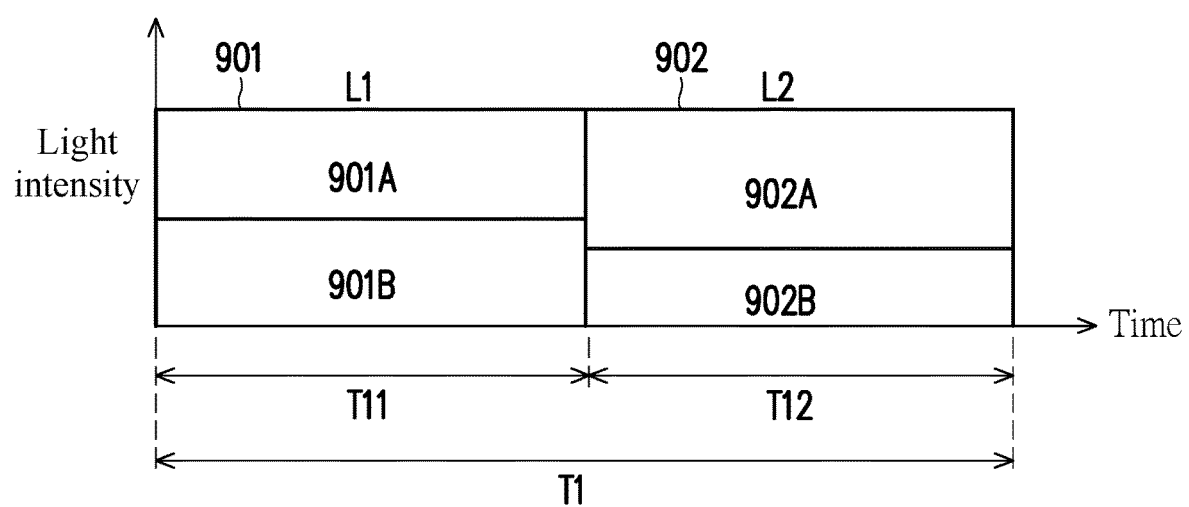
FIG. 9 to FIG. 11 are optical signal timing diagrams according to some embodiments of the disclosure.

FIG. 9 is an optical signal timing diagram according to some embodiments of the disclosure. According to some embodiments, the first light source 110 and the second light source 120 in FIG. 1 may have the same or different phosphor compositions, so two different light beams may be emitted at the same time, for example, a combination of white light and blue light, and the disclosure is not limited thereto. As shown in FIG. 9, in the first time period T11 of the first period T1, a first light beam 901 emitted by the first light source 110 is a combination of white light 901A and blue light 901B. In the second time period T12 of the first period T1, a second light beam 902 emitted by the second light source 120 is a combination of white light 902A and blue light 902B. According to some embodiments, the light intensity difference between the first light beam 901 and the second light beam 902 is less than a threshold, for example, less than 10% or less. The light intensity of the first light beam 901 is the sum of the light intensities of the white light 901A and the blue light 901B, and the light intensity of the second light beam 902 is the sum of the light intensities of the white light 902A and the blue light 902B. According to some embodiments, the white light 901A of the first light beam 901 and the white light 902A of the second light beam 902 may have the same color temperature and the same or different spectra, and the disclosure is not limited thereto. According to some embodiments, the blue light 901B of the first light beam 901 and the blue light 902B of the second light beam 902 may have the same color temperature and the same or different spectra, and the disclosure is not limited thereto. According to some embodiments, a light intensity ratio of the white light 901A to the blue light 901B in the first light beam 901 may be the same as or different from a light intensity ratio of the white light 902A to the blue light 902B in the second light beam 902, and the disclosure is not limited thereto. The combinations of the white light and the blue light of the first light beam 901 and the second light beam 902 described in the embodiment may be applied to the foregoing embodiments and are not limited thereto.

Figure 10:
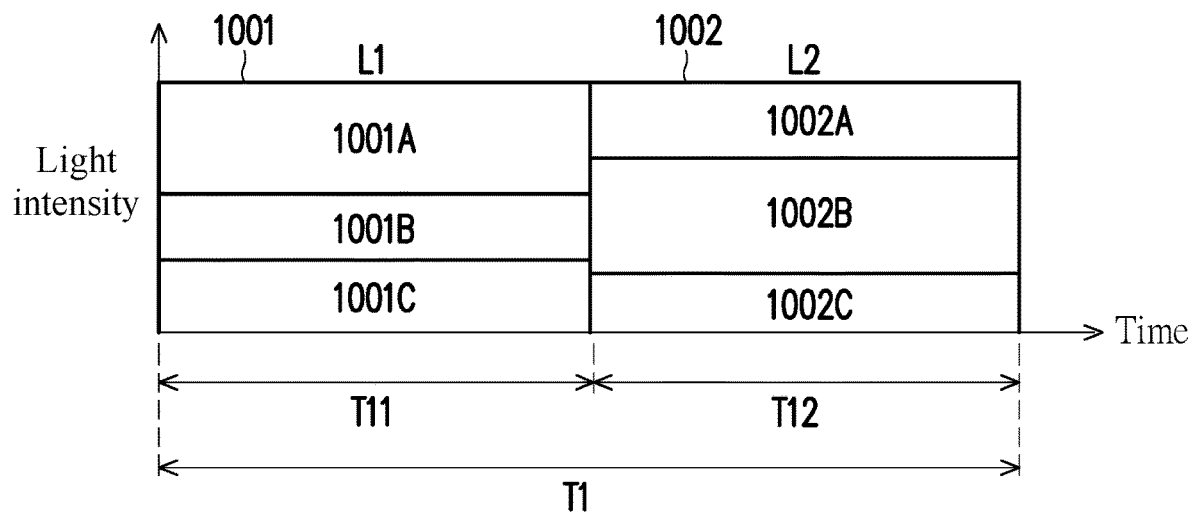

FIG. 10 is an optical signal timing diagram according to some embodiments of the disclosure. According to some embodiments, the first light source 110 and the second light source 120 in FIG. 1 may have the same or different light source compositions, so a combination of blue light, green light, and red light may be emitted. As shown in FIG. 10, in the first time period T11 of the first period T1, a first light beam 1001 emitted by the first light source 110 is a combination of blue light 1001A, green light 1001B, and red light 1001C. In the second time period T12 of the first period T1, a second light beam 1002 emitted by the second light source 120 is a combination of blue light 1002A, green light 1002B, and red light 1002C. According to some embodiments, the light intensity difference between the first light beam 1001 and the second light beam 1002 is less than a threshold, for example, less than 10% or less. The light intensity of the first light beam 1001 is the sum of the light intensities of the blue light 1001A, the green light 1001B, and the red light 1001C, and the light intensity of the second light beam 1002 is the sum of the light intensities of the blue light 1002A, the green light 1002B, and the red light 1002C. According to some embodiments, the blue light 1001A of the first light beam 1001 and the blue light 1002A of the second light beam 1002 may have the same color temperature and the same or different spectra, and the disclosure is not limited thereto. According to some embodiments, the green light 1001B of the first light beam 1001 and the green light 1002B of the second light beam 1002 may have the same color temperature and the same or different spectra, and the disclosure is not limited thereto. According to some embodiments, the red light 1001C of the first light beam 1001 and the red light 1002C of the second light beam 1002 may have the same color temperature and the same or different spectra, and the disclosure is not limited thereto. According to some embodiments, a light intensity ratio of the blue light 1001A to the green light 1001B to the red light 1001C in the first light beam 1001 may be the same as or different from a light intensity ratio of the blue light 1002A to the green light 1002B to the red light 1002C in the second light beam 1002, and the disclosure is not limited thereto. The combinations of the blue light, the green light, and the red light of the first light beam 1001 and the second light beam 1002 described in the embodiment may be applied to the foregoing embodiments and are not limited thereto.

Figure 11:
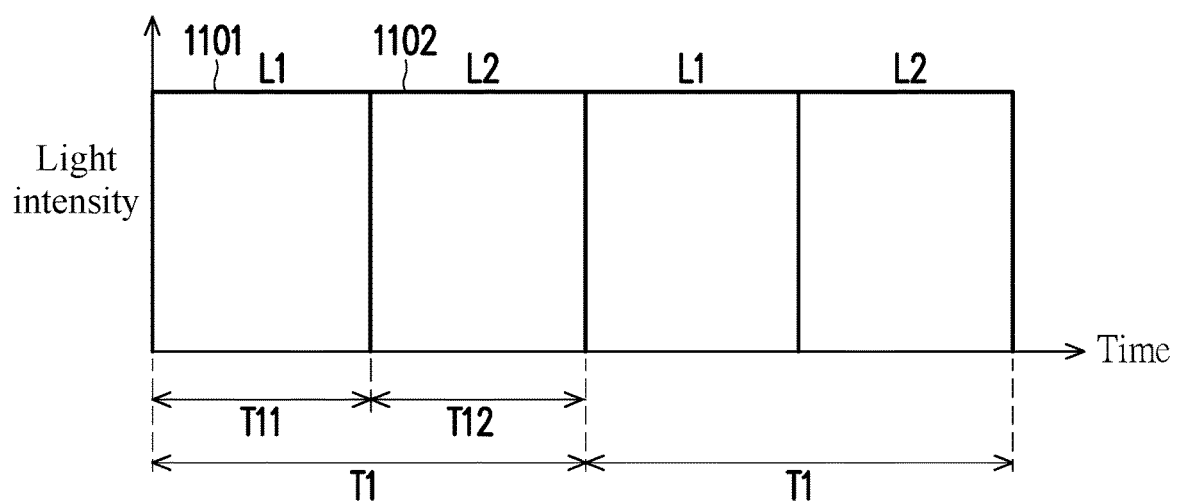

FIG. 11 is an optical signal timing diagram according to some embodiments of the disclosure. According to some embodiments, the first light source 110 and the second light source 120 in FIG. 1 respectively emit monochromatic light or white light, wherein when the color of a single light is within 4 McAdam ellipses in the same x and y coordinate range, there may be different spectra. Therefore, the periodic changes of two different spectra may be used to modulate new light. As shown in FIG. 11, in the first time period T11 of the first period T1, the first light source 110 emits a first light beam 1101, and in the second time period T12 of the first period T1, the second light source 120 emits a second light beam 1102. According to some embodiments, the spectra of the first light beam 1101 and the second light beam 1102 are different, and a color coordinate difference is within 4 MacAdam ellipses. According to some embodiments, when the light source device 100 is applied to a display, the light intensities of the first light beam 1101 and the second light beam 1102 are the same, ot the light intensity difference between the first lgiht beam 1101 and the second light beam 1102 is less than 10%. According to some embodiments, when the light source device 100 is applied to external light stimulation, the light intensities of the first light beam 1101 and the second light beam 1102 are different. The combinations of the first light beam 1101 and the second light beam 1102 described in the embodiment may be applied to the foregoing embodiments and are not limited thereto. Regardless of whether the white light is composed of a single light source or dual light sources, the higher the color rendering index, the better the response to the user, especially when CRI>85.

Figure 12:
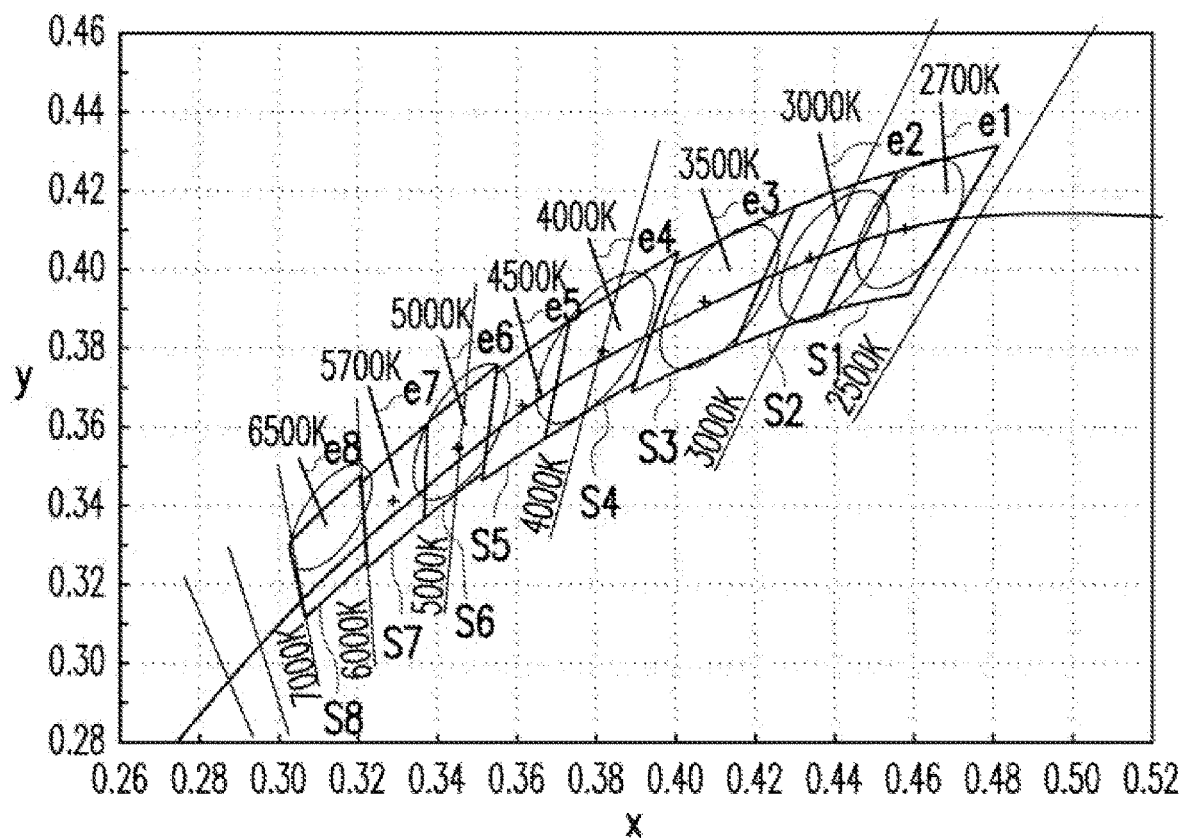
FIG. 12 is a schematic diagram of color coordinate configurations of the same color temperature defined by the American National Standards Institute.

FIG. 12 is a schematic diagram of color coordinate configurations of the same color temperature defined by the American National Standards Institute (ANSI). Please refer to FIG. 12. In the embodiment, the definition of the same color temperature is in accordance with the definition of the ANSI. In other words, for light sources with the same color temperature designed according to the standard, the color difference is not easily perceivable to the human eye. Please refer to Table 1 below for the detailed coordinate values of the color coordinate configurations defined by the ANSI as shown in the schematic diagram of FIG. 12:

TABLE 1

| | X | Y | X | Y | X | Y | X | Y |
|---|---|---|---|---|---|---|---|---|
| | 2700k | | 3000k | | 3500k | | 4000k | |
| Center point | 0.4578 | 0.4101 | 0.4338 | 0.4030 | 0.4073 | 0.3917 | 0.3818 | 0.3797 |
| Tolerance | 0.4813 | 0.4319 | 0.4562 | 0.4260 | 0.4299 | 0.4165 | 0.4006 | 0.4044 |
| quadrilateral | 0.4562 | 0.4260 | 0.4299 | 0.4165 | 0.3996 | 0.4015 | 0.3736 | 0.3874 |
| | 0.4373 | 0.3893 | 0.4147 | 0.3814 | 0.3889 | 0.3690 | 0.3670 | 0.3578 |
| | 0.4593 | 0.3944 | 0.4373 | 0.3893 | 0.4147 | 0.3814 | 0.3898 | 0.3716 |

TABLE 1-continued

| | X | Y | X | Y | X | Y | X | Y |
|---|---|---|---|---|---|---|---|---|
| | 4500k | | 5000k | | 5700k | | 6500k | |
| Center point | 0.3611 | 0.3658 | 0.3447 | 0.3553 | 0.3287 | 0.3417 | 0.3123 | 0.3282 |
| Tolerance | 0.3736 | 0.3874 | 0.3551 | 0.3760 | 0.3376 | 0.3616 | 0.3205 | 0.3481 |
| quadrilateral | 0.3548 | 0.3736 | 0.3376 | 0.3616 | 0.3207 | 0.3462 | 0.3028 | 0.3304 |
| | 0.3512 | 0.3465 | 0.3366 | 0.3369 | 0.3222 | 0.3243 | 0.3068 | 0.3113 |
| | 0.3670 | 0.3578 | 0.3515 | 0.3487 | 0.3366 | 0.3369 | 0.3221 | 0.3261 |

The data range of Table 1 may be converted into tolerance quadrilateral color temperature ranges S1 to S8 in FIG. 12. For example, color temperature coordinate values in the tolerance quadrilateral color temperature range S1 are very close to the human eye, and so on. In more detail, the tolerance quadrilateral in Table 1 may be further converted into the color temperature range as shown in Table 2 below:

TABLE 2

| Correlated color temperature (CCT) | Target-related color temperature (K) and tolerance |
|---|---|
| 2700k | 2725 ± 145 |
| 3000k | 3045 ± 175 |
| 3500k | 3465 ± 245 |
| 4000k | 3985 ± 275 |
| 4500k | 4503 ± 243 |
| 5000k | 5028 ± 283 |
| 5700k | 5665 ± 355 |
| 6500k | 6530 ± 510 |

The data range of Table 2 may be converted into elliptical color temperature ranges e1 to e8 in FIG. 3. Further, the elliptical color temperature ranges e1 to e8 are also referred to as MacAdam ellipses. For example, color temperature coordinate values fallen within the elliptical color temperature range e1 are very close to the human eye, and so on. It is worth noting that the coordinate data in Table 1 and Table 2 are examples to illustrate that the color temperatures in the embodiment are substantially the same. Please refer to the latest definition of the ANSI for actual coordinate data, and the disclosure is not limited thereto. In another embodiment, having substantially the same color temperature represents being in the same elliptical color temperature range. In this way, the light source device 100 may select light sources with different circadian action factors (CAFs) according to the actual use environment, time, and purpose in the case where the user cannot easily perceive changes in light color temperature to maintain the physiological period of the user, while providing sufficient light source.

Figure 13A:
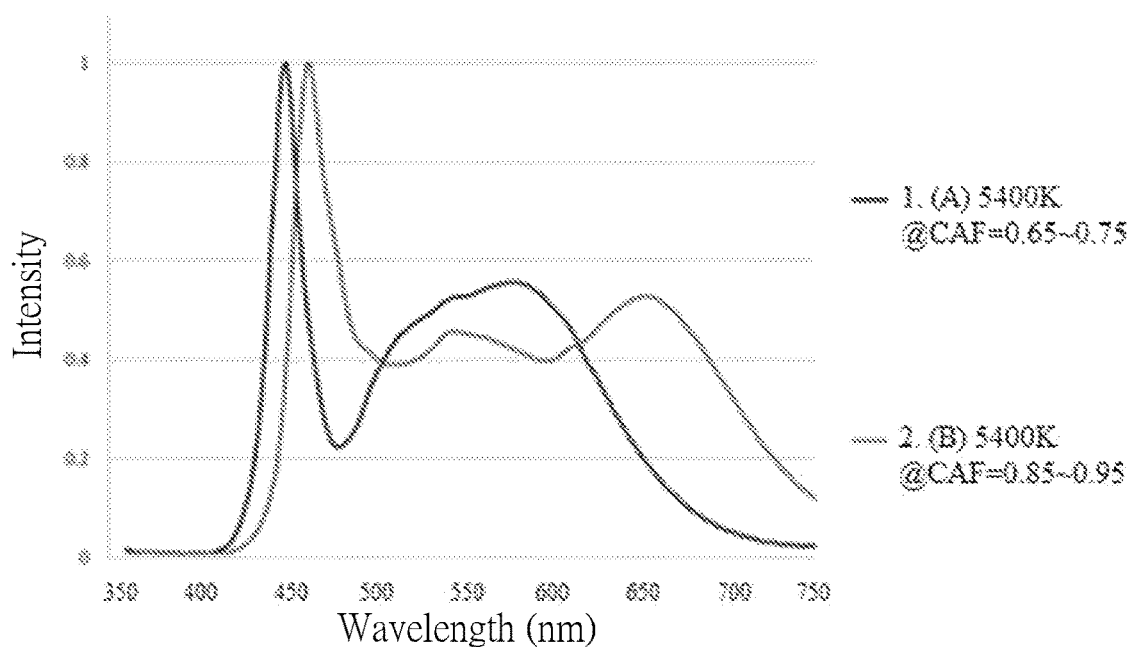
FIG. 13A and FIG. 13B are spectral distributions with the same color temperature according to some embodiments of the disclosure.
Figure 13B:
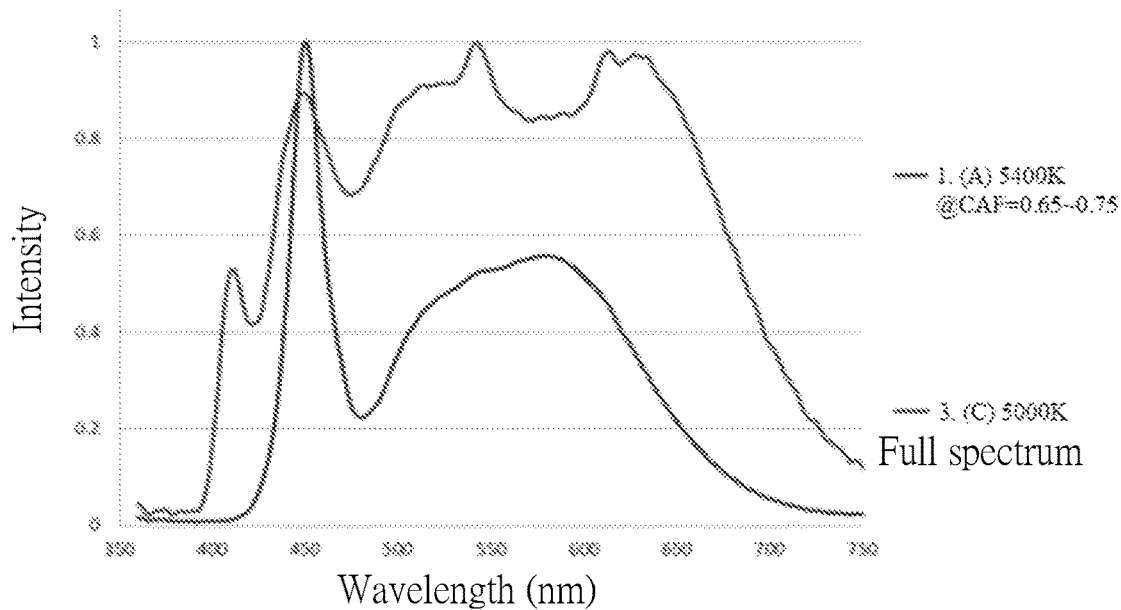

FIG. 13A and FIG. 13B are spectral distributions according to some embodiments of the disclosure. As shown in FIG. 13A, a spectrum (A) and a spectrum (B) have the same color temperature. In the embodiment, the color temperature of the spectrum (A) is 5529K, and the color temperature of the spectrum (B) is 5400K, but the spectra have different spectral distributions. The intensity peak of the spectrum (A) is approximately at a wavelength of 450 nm, and the intensity peak of the spectrum (B) is approximately at a wavelength of 460 nm. The color rendering index of the spectrum (A) is 81, the color rendering index of the spectrum (B) is 86, and the color rendering index of the spectrum (A) and the spectrum (B) after mixing is 86. As shown in FIG. 13A, a CAF range of the spectrum (A) is CAF=0.65-0.75 and a CAF range of the spectrum (B) is CAF=0.85-0.95. Therefore, in the case of the same color temperature, light with different spectra have different CAFs.

As shown in FIG. 13B, the two spectra in the drawing are respectively the spectrum (A) and a spectrum (C). The color temperature of the spectrum (C) is 4919K, and the spectrum (C) is a full spectrum in a wavelength range of 400-7000 nm, so the color rendering index of the spectrum (C) is 97. The color rendering index of the spectrum (A) and the spectrum (C) after mixing is 90.

Figure 14A:
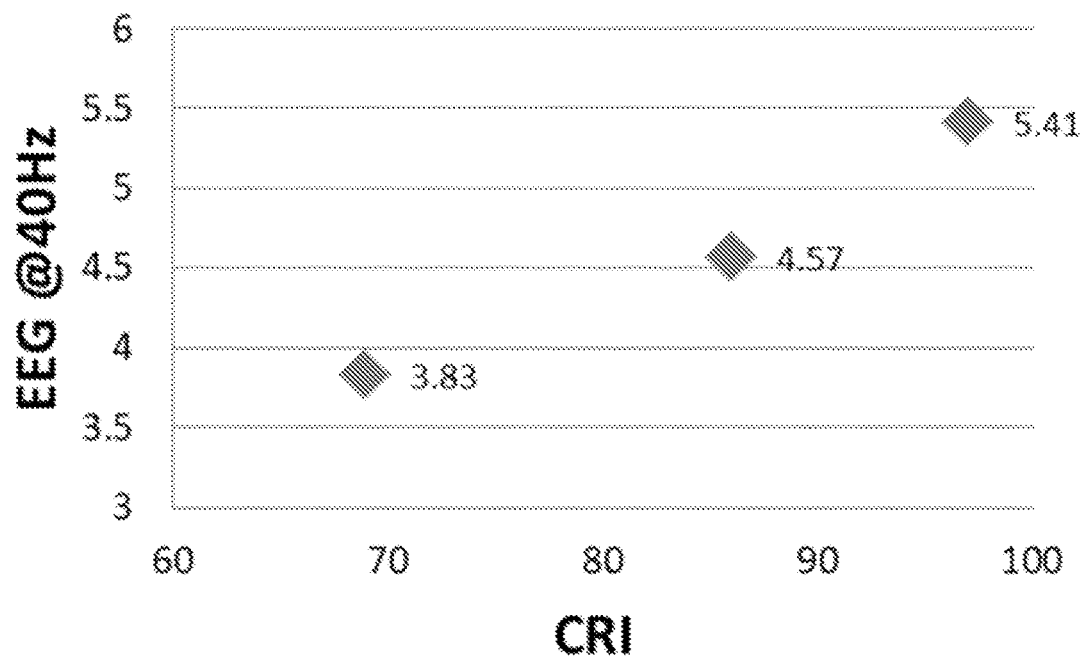
FIG. 14A and FIG. 14B show a relationship between a color rendering index and an electroencephalography signal according to some embodiments of the disclosure.
Figure 14B:
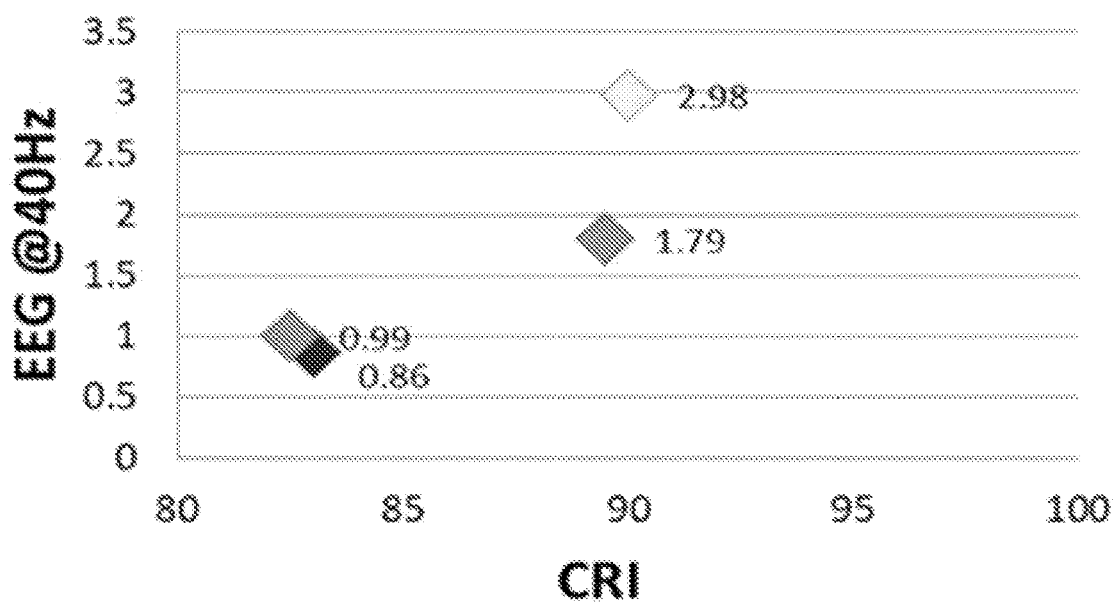

FIG. 14A and FIG. 14B show a relationship between a color rendering index and an electroencephalography (EEG) signal according to some embodiments of the disclosure. FIG. 14A uses a single light source to flicker at a fixed flicker frequency. In the embodiment, the flicker frequency is 40 Hz to measure the signal intensity of the EEG at 40 Hz in different color rendering indexes. In FIG. 14A, the color temperature of a light source is around 5000K. When the color rendering index of the light source gradually increases from 60 to close to 100, the signal of the EEG at 40 Hz is also correspondingly enhanced, which means that the higher the color rendering index of the light source, the better the response to the user, especially when the color rendering index, CRI≥85, the signal intensity is above 4, which means that the signal intensity is more significant than when the color rendering index, CRI<85.

FIG. 14B is similar to FIG. 14A, but FIG. 14B uses dual light sources to flicker alternately at a fixed flicker frequency. In the embodiment, the flicker frequency is 40 Hz to measure the signal intensity of the EEG at 40 Hz. As shown in FIG. 14B, when the color rendering index of the light source is less than 85, the signal (0.86-0.99) of the EEG at 40 Hz is significantly less than the signal (>1.79) of the EEG at 40 Hz when the color rendering index of the light source is greater than 85, which means that the higher the color rendering index of the light source, the better the response to the user. It can be seen from FIG. 14B that when the color rendering index, CRI≥85, the signal intensity is above 1.5, which means that the signal intensity is more significant than when the color rendering index, CRI<85.

In FIG. 14A and FIG. 14B, when CRI≥85, the EEG signal intensity (>4) of FIG. 14A is stronger than the EEG signal intensity (1.79-2.98) of FIG. 14B. Since FIG. 14A uses the single light source to flicker, the brightness difference is more obvious, and the obtained EEG signal is stronger. In FIG. 14B, since the dual light sources are used to flicker alternately, the brightness difference is less obvious, and the obtained EEG signal is weaker than the EEG signal when the single light source flickers (as shown in FIG. 14A). However, in actual use, when using a single light source to flicker, since the brightness contrast is more obvious, there is a greater burden on the eyes of the user. When using dual light sources to flicker, since the brightness change is smaller, there is hardly any burden on the eyes of the user, which is more suitable for integration into the daily life environment.

Figure 15A:
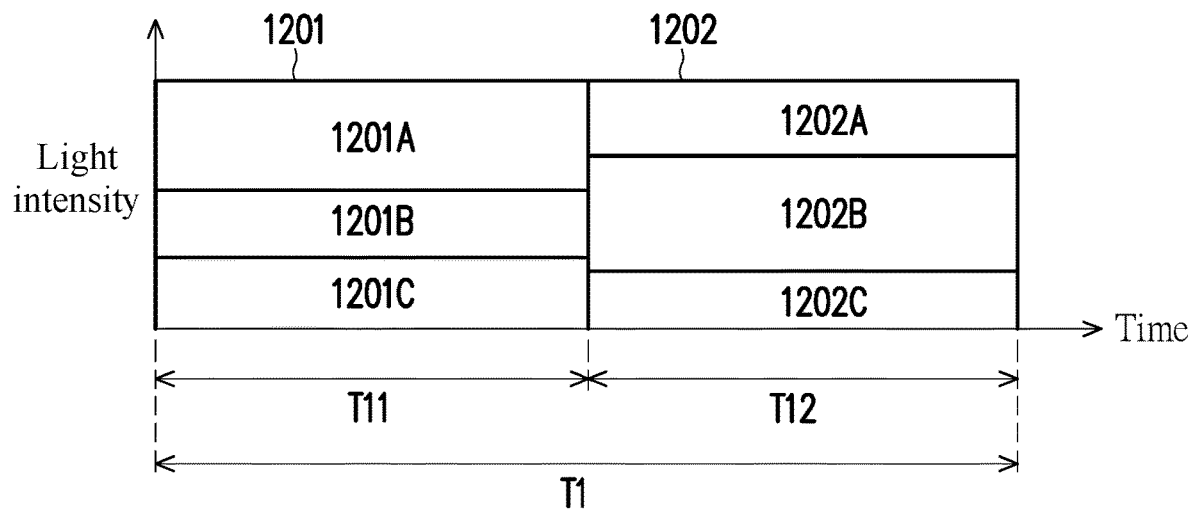
FIG. 15A to FIG. 15B are optical signal timing diagrams according to some embodiments of the disclosure.
Figure 15B:
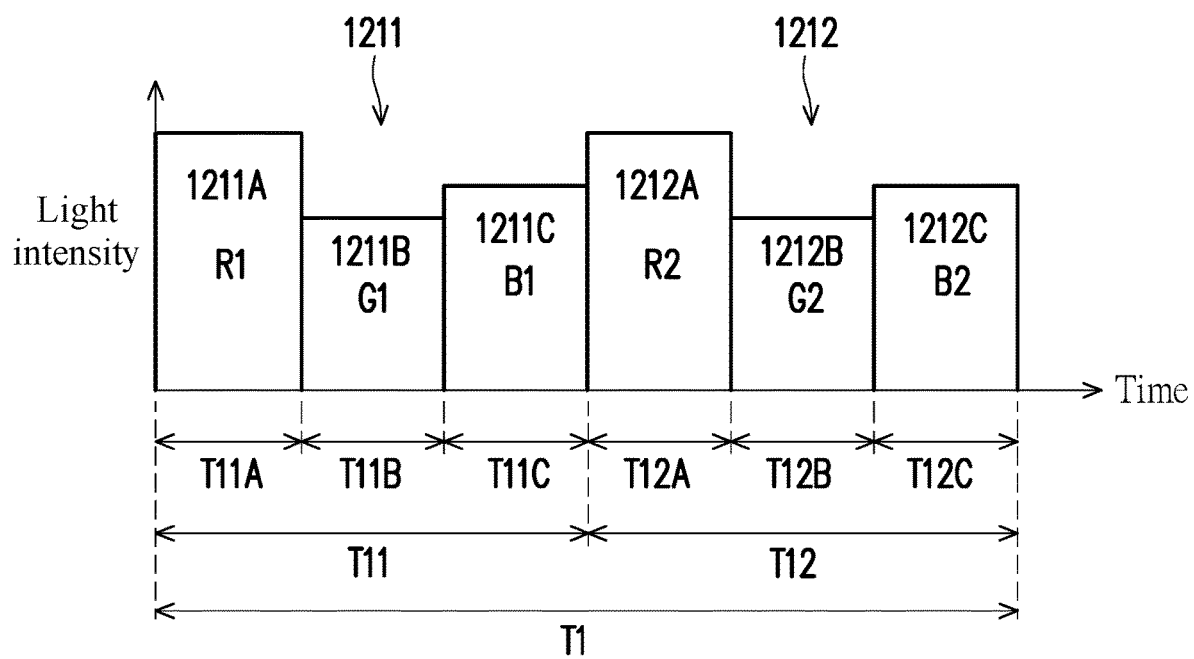

FIG. 15A to FIG. 15B are optical signal timing diagrams according to some embodiments of the disclosure. According to some embodiments, a single display pixel in the first light source 110 and the second light source 120 in FIG. 1 has periodic changes of different monochromatic light combinations. At this time, the single display pixel may have two different change combinations, such as emitting different monochromatic light at the same time or sequentially emitting different monochromatic light. As shown in FIG. 15A, in the first time period T11 of the first period T1, the first light source 110 emits red light 1201A, green light 1201B, and blue light 1201C at the same time. In the second time period T12 of the first period T1, the second light source 120 emits red light 1202A, green light 1202B, and blue light 1202C at the same time. As shown in FIG. 15B, in a first part T11A, a second part T11B, and a third part T11C of the first time period T11 of the first period T1, the first light source 110 sequentially emits red light 1211A, green light 1211B, and blue light 1211C. In a first part T12A, a second part T12B, and a third part T12C of the second time period T12 of the first period T1, the second light source 120 sequentially emits red light 1212A, green light 1212B, and blue light 1212C. According to some embodiments, the wavelengths of the red light 1211A and the red light 1212B are different, and the color coordinate difference may be within 4 MacAdam ellipses. According to some embodiments, the wavelengths of the green light 1211B and the green light 1212B are different, and the color coordinate difference may be within 4 MacAdam ellipses. According to some embodiments, the wavelengths of the blue light 1211C and the blue light 1212C are different, and the color coordinate difference may be within 4 MacAdam ellipses. According to some embodiments, when the light source device 100 is applied to a display, the light intensities of a first light beam 1201 and a second light beam 1202 are the same. According to some embodiments, when the light source device 100 is applied to external light stimulation, the light intensities of the first light beam 1201 and the second light beam 1202 are different. The combinations of the first light beam 1201 and the second light beam 1202 described in the embodiment may be applied to the foregoing embodiments and are not limited thereto.

Figure 16:
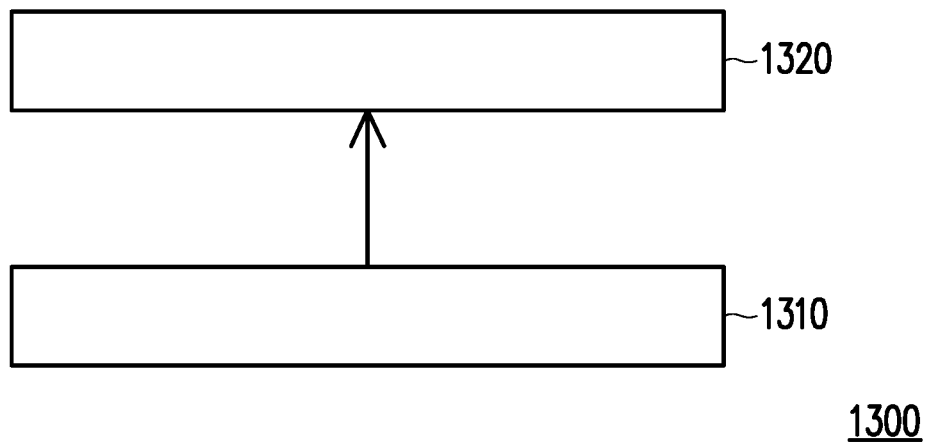
FIG. 16 is a schematic diagram of a display device according to some embodiments of the disclosure.

FIG. 16 is a schematic diagram of a display device according to some embodiments of the disclosure. Please refer to FIG. 16. A display device 1300 of the embodiment includes a backlight element 1310 and a display 1320. The display 1320 may be a liquid crystal display panel or other suitable spatial light modulators. The backlight element 1310 may be the various embodiments of the light source device 100 described above and is configured to provide backlight of the display 1320. According to some embodiments, the backlight element 1310 is a direct-type backlight element or an edge-type backlight element, and the disclosure is not limited thereto. When the backlight element 1310 includes the various embodiments of the light source device 100 described above, a light period of the backlight of the display is composed of two different light. Therefore, when the user uses the display, light stimulation may be received at the same time. In another embodiment, a light source of the display device is a light emitting unit of the display, and light emitted by each light emitting unit is alternately emitted in the time of one period as described the foregoing embodiments.

Figure 17:
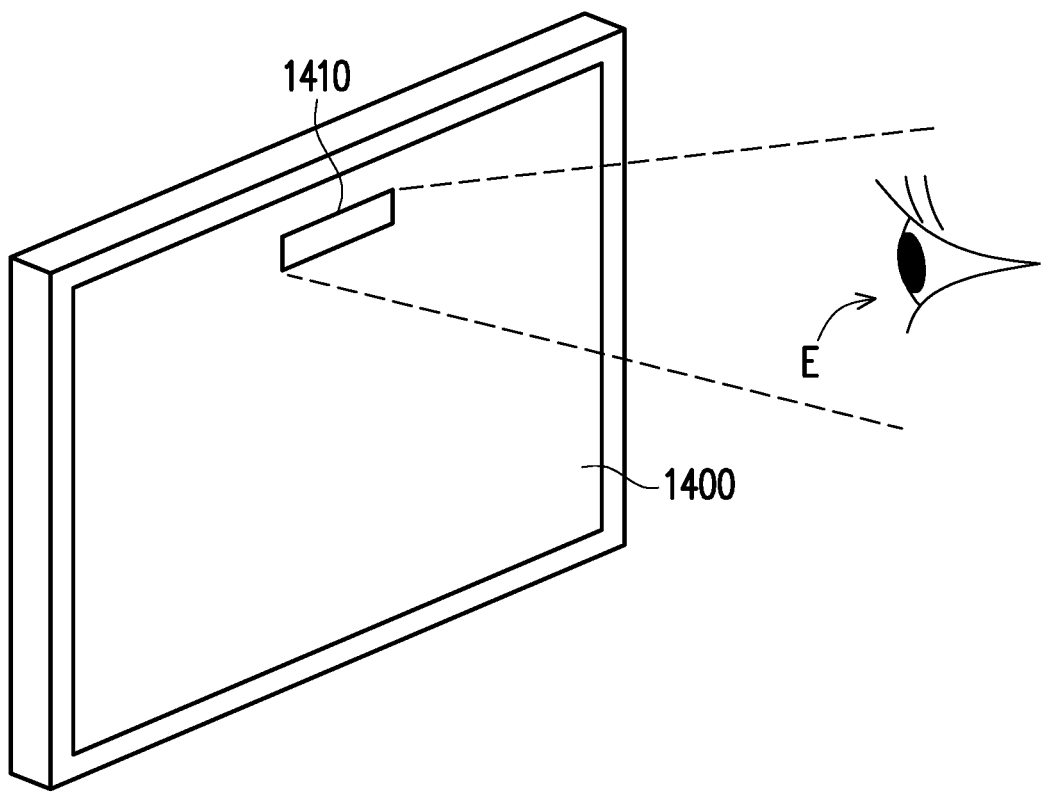
FIG. 17 is a schematic diagram of a display device according to some embodiments of the disclosure.

FIG. 17 is a schematic diagram of a display device according to some embodiments of the disclosure. As shown in FIG. 17, a display device 1400 has a light source device 1410. The light source device 1410 is similar to the light source device 100 in FIG. 1 and may emit two different light alternately in one period. In the embodiment, a light beam emitted by the light source device 1410 is infrared light.

In some embodiments, the light source device or the display device described above may be further combined with an eye movement sensor to track the movement of an eye portion E of the user. The light source device 1410 may generate the infrared light with a flicker frequency of 40 Hz corresponding to the first period to provide stimulation of the infrared light or other invisible light with a flicker frequency of 40 Hz around the line of sight of the user.

In summary, the disclosure uses a combination of two or more light to be emitted alternately in the time of one period to provide light stimulation with therapeutic effects. The combination of different forms of light can effectively provide a variety of treatment measures.

What is claimed is:

1. A light source device, comprising:
   a first light source, providing a first light beam in a first time period of a first period;
   a second light source, providing a second light beam in a second time period of the first period;
   a third light source, providing a third light beam in a third time period of a second period; and
   a fourth light source, providing a fourth light beam in a fourth time period of the second period, wherein
   the first light beam and the second light beam are emitted alternately in the first period, and a color rendering index of mixed light of the first light beam and the second light beam is greater than or equal to 85,
   the third light beam and the fourth light beam are emitted alternately in the second period.

2. The light source device according to claim 1, wherein the first light beam and the second light beam have different spectra.

3. The light source device according to claim 2, wherein the first light beam and the second light beam have a same color temperature.

4. The light source device according to claim 2, wherein at least one of the first light beam and the second light beam is a full spectrum light beam.

5. The light source device according to claim 1, wherein at least one of the first light beam in the first time period and the second light beam in the second time period is a continuous light beam.

6. The light source device according to claim 1, wherein at least one of the first light beam in the first time period and the second light beam in the second time period is a flicker light beam.

7. The light source device according to claim 6, wherein a flicker frequency range of the flicker light beam is 500-2000 Hz.

8. The light source device according to claim 1, wherein the first light beam in the first time period and the second light beam in the second time period are both flicker light beams, and a first flicker frequency of the first light beam is different from a second flicker frequency of the second light beam.

9. The light source device according to claim 1, wherein a sum of a duration of the first time period and a duration of the second time period is equal to a duration of the first period.

10. The light source device according to claim 1, wherein a frequency corresponding to the first period is 35-45 Hz.

11. The light source device according to claim 1, wherein the first light beam and the second light beam have different light intensities.

12. The light source device according to claim 11, wherein a light intensity difference between the first light beam and the second light beam is less than 10%.

13. The light source device according to claim 1, further comprising a sound source, generating a sound wave pulse, wherein an emission period of the sound wave pulse is same as the first period.

14. The light source device according to claim 1, wherein a wavelength of at least one of the first light beam and the second light beam is within a range of 380-1050 nm.

15. The light source device according to claim 1, wherein at least one of the first light beam and the second light beam is a monochromatic light beam.

16. The light source device according to claim 1, wherein at least one of the first light beam and the second light beam is a mixed light beam.

17. The light source device according to claim 16, wherein the mixed light comprises red light, blue light, and green light.

18. The light source device according to claim 16, wherein the mixed light comprises white light and blue light.

19. The light source device according to claim 1, wherein the third light beam and the fourth light beam have a same color temperature.

20. The light source device according to claim 1, wherein a color rendering index of mixed light of the third light beam and the fourth light beam is greater than or equal to 85.

21. The light source device according to claim 1, wherein a frequency corresponding to the second period is different from a frequency corresponding to the first period.

22. The light source device according to claim 1, wherein the third light beam and the fourth light beam have different light intensities.

23. The light source device according to claim 1, wherein the third light beam and the fourth light beam have different spectra.

24. A display device, comprising a light source device, wherein the light source device comprises:
a first light source, providing a first light beam in a first time period of a first period;
a second light source, providing a second light beam in a second time period of the first period;
a third light source, providing a third light beam in a third time period of a second period; and
a fourth light source, providing a fourth light beam in a fourth time period of the second period, wherein
the first light beam and the second light beam are emitted alternately in the first period, and a color rendering index of mixed light of the first light beam and the second light beam is greater than or equal to 85,
the third light beam and the fourth light beam are emitted alternately in the second period.

25. A light source device, comprising:
a first light source, providing a first light beam in a first time period of a first period;
a second light source, providing a second light beam in a second time period of the first period;
a third light source, providing a third light beam in a third time period of a second period; and
a fourth light source, providing a fourth light beam in a fourth time period of the second period, wherein
the first light beam and the second light beam are emitted alternately in the first period, and the first light beam and the second light beam have a same color temperature,
wherein a color rendering index of mixed light of the first light beam and the second light beam is greater than or equal to 85,
wherein the third light beam and the fourth light beam are emitted alternately in the second period.

26. A light source device, comprising:
a first light source, providing a first light beam in a first time period of a first period;
a second light source, providing a second light beam in a second time period of the first period;
a third light source, providing a third light beam in a third time period of a second period; and
a fourth light source, providing a fourth light beam in a fourth time period of the second period, wherein
the first light beam and the second light beam are emitted alternately in the first period, when a color rendering index of mixed light of the first light beam and the second light beam is greater than or equal to 85, an electroencephalography response of a user is greater than the electroencephalography response of the user when the color rendering index of the mixed light of the first light beam and the second light is smaller than 85,
the third light beam and the fourth light beam are emitted alternately in the second period.

* * * * *